United States Patent [19]

Kennis et al.

[11] Patent Number: 4,529,727
[45] Date of Patent: Jul. 16, 1985

[54] PYRIMIDO[2,1-b][1,3]-THIAZINES

[75] Inventors: Ludo E. J. Kennis, Turnhout; Josephus C. Mertens, Oud-Turnhout, both of Belgium

[73] Assignee: Janssen Pharmaceutical, N.V., Beerse, Belgium

[21] Appl. No.: 576,291

[22] Filed: Feb. 2, 1984

Related U.S. Application Data

[60] Division of Ser. No. 370,653, Apr. 21, 1982, Pat. No. 4,443,451, which is a continuation-in-part of Ser. No. 283,590, Jul. 15, 1981, abandoned.

[51] Int. Cl.³ .................. C07D 417/14; A61K 31/38; A61K 31/445
[52] U.S. Cl. ........................................ 514/226; 544/48
[58] Field of Search ........................... 544/48; 424/246

[56] References Cited

U.S. PATENT DOCUMENTS

| 2,464,780 | 3/1949 | Anish | 544/48 |
| 3,646,022 | 2/1972 | Graf et al. | 544/48 |
| 3,740,394 | 6/1973 | Baetz | 544/48 |
| 3,910,941 | 10/1975 | Turner | 544/48 |
| 4,485,107 | 11/1984 | Kennis et al. | 544/48 |

FOREIGN PATENT DOCUMENTS 58-55482  4/1983  Japan ............................... 544/48

Primary Examiner—John M. Ford
Attorney, Agent, or Firm—Geoffrey G. Dellenbaugh

[57] ABSTRACT

Novel 5H-thiazolo- and 5H-1,3,4-thiadiazolo[3,2-a]pyrimidin-5-one and 3,4-dihydro-2H,6H-pyrimido[2,1-b][1,3]-thiazin-6-one derivatives, which compounds are useful psychotropic agents.

6 Claims, No Drawings

PYRIMIDO[2,1-B][1,3]-THIAZINES

CROSS-REFERENCE TO RELATED APPLICATIONS

This application is a division of our copending application Ser. No. 370,653, filed Apr. 21, 1982, now U.S. Pat. 4,443,451, which in turn is a continuation-in-part of application Ser. No. 283,590, filed July 15, 1981, now abandoned.

BACKGROUND OF THE INVENTION

In Japanese Kokai No. 7 6146-497 and in Ann. Rep. Sankyo Res. Lab. 29, 75–98 (1977) there are described a number of 4H-pyrido[1,2-a]pyrimidin-4-one derivatives, bearing in the 3-position an aminoalkyl substituent, wherein the amino group may be part of a morpholino-, a piperidino- or a piperazine moiety, which compounds are taught to be useful as cardiovascular agents and as agents acting on the central nervous system.

In the European Patent application having the publication No. 37,265 there are described a number of 3-(1-piperidinylalkyl)-4H-pyrido[1,2-a]pyrimidin-4-one derivatives wherein the piperidine ring is substituted with an aroyl radical or a functional derivative thereof, which compounds are potent serotonin-antagonists.

The compounds of the present invention differ from the prior art compounds by the substitution of the 4H-pyrido[1,2-a]pyrimidin-4-one group by a 5H-thiazolo[3,2-a]pyrimidin-5-one, a 5H-1,3,4-thiadiazolo[3,2-a]pyrimidin-5-one or a 3,4-dihydro-2H,6H-pyrimido[2,1-b][1,3]thiazin-6-one group and by their useful properties in the treatment of psychotropic diseases.

DESCRIPTION OF THE PREFERRED EMBODIMENTS:

This invention is concerned with piperidine derivatives which are structurally represented by the formula

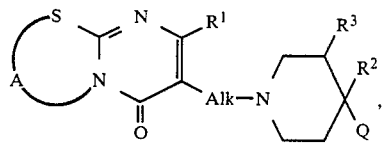

the pharmaceutically acceptable acid-addition salts and the stereochemically isomeric forms thereof, wherein:

$R^1$ is hydrogen, lower alkyl or Ar;
$R^2$ is hydrogen, lower alkyl or Ar;
$R^3$ is hydrogen or lower alkyl;
Alk is a lower alkanediyl radical;
A is a bivalent radical having the formula

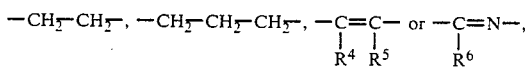

having the carbon atom attached to the S-atom, wherein $R^4$, $R^5$ and $R^6$ are each independently selected from the group consisting of hydrogen and lower alkyl and wherein $R^4$ and $R^5$ may also complete a saturated or unsaturated 5- or 6-membered carbocyclic ring, optionally substituted with a lower alkyl radical; and Q is a member selected from the group consisting of a radical having the formula —X—Ar (a) wherein X is a member selected from the group consisting of

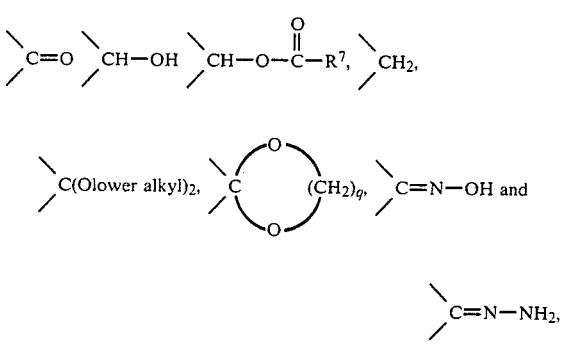

said $R^7$ being hydrogen or lower alkyl and said q being the integer 2 or 3; and a radical having the formula

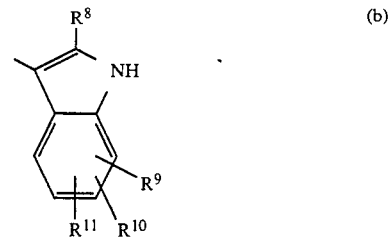

wherein $R^8$ is hydrogen or lower alkyl and $R^9$, $R^{10}$ and $R^{11}$ are each independently selected from the group consisting of hydrogen and halo; wherein Ar is phenyl or substituted phenyl, said substituted phenyl bearing an amino group and/or 1,2 or 3 halo atoms.

As used in the foregoing definitions the term "halo" is generic to fluoro, chloro, bromo and iodo; "lower alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; and "lower alkanediyl", as used in the definition of Alk, comprises straight and branched saturated alkanediyl chains having from 1 to 4 carbon atoms.

Preferred compounds within the scope of formula (I) are those wherein $R^1$ is lower alkyl.

More particularly preferred compounds within the scope of formula (I) are those wherein $R^1$ is lower alkyl, A is other than —CH$_2$—CH$_2$—CH$_2$—, Q is a radical of formula (a) wherein X is >C=O or a radical of formula (b) wherein $R^9$, $R^{10}$ and $R^{11}$ are hydrogen, Ar is other than aminophenyl, $R^2$ is hydrogen or lower alkyl and $R^3$ is hydrogen.

The most preferred compounds within the scope of formula (I) are selected from the group consisting of 6-[2-[4-(4-fluorobenzoyl)-1-piperidinyl]ethyl]-3,7-dimethyl-5H-thiazolo[3,2-a]pyrimidin-5-one; 6-[2-[4-(4-fluorobenzoyl)-1-piperidinyl]ethyl]-2,3-dihydro-7-methyl-5H-thiazolo[3,2-a]pyrimidin-5-one and 6-[2-[4-(1H-indol-3-yl)-1-piperidinyl]ethyl]-3,7-dimethyl-5H-thiazolo[3,2-a]pyrimidin-5-one, the pharmaceutically acceptable acid addition salts and the stereochemically isomeric forms thereof.

The compounds of formula (I) can generally be prepared by reacting an appropriate reactive ester of formula (II) with an appropriately substituted piperidine of formula (III). In the reactive ester (II) A, $R^1$ and Alk are as previously described and W represents a reactive leaving group such as, for example, halo, particularly, chloro, bromo and iodo, or a sulfonyloxy group, e.g., methylsulfonyloxy, 4-methylphenylsulfonyloxy and the like. In the piperidine (III) $R^2$, $R^3$ and Q are as previously described.

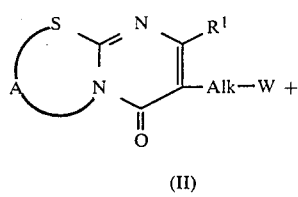

(II)

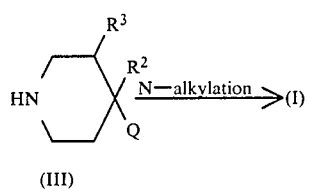

(III)

The foregoing reaction may be carried out following standard N-alkylating procedures. Said reaction is preferably carried out in an appropriate reaction-inert solvent such as, for example, a lower alkanol, e.g., methanol, ethanol, propanol, butanol and the like alkanols; an aromatic hydrocarbon, e.g., benzene, methylbenzene, dimethylbenzene, and the like; an ether, e.g., 1,4-dioxane, 1,1'-oxybispropane and the like; a ketone, e.g., 4-methyl-2-pentanone; N,N-dimethylformamide; nitrobenzene; and the like. The addition of an appropriate base such as, for example, an alkali or earth alkaline metal carbonate or hydrogen carbonate, may be utilized to pick up the acid which is liberated during the course of the reaction. A small amount of an appropriate metal iodide, e.g., sodium or potassium iodide may be added as a reaction promotor. Somewhat elevated temperatures are appropriate to enhance the rate of the reaction and preferably the reaction is carried out at the reflux temperature of the reaction mixture.

The compounds of formula (I) can also be prepared following art-known cyclizing procedures for preparing pyrimidin-4-ones such as, for example, by reacting an amine of formula (IV) with a cyclizing agent of formula (V) or by cyclizing a reagent of formula (VI) with an amine of formula (VII).

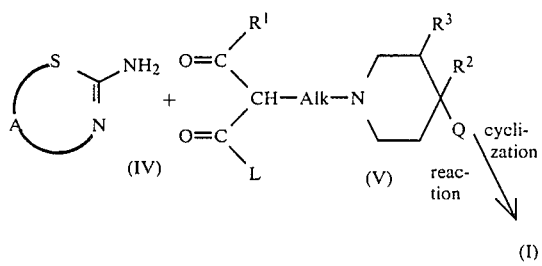

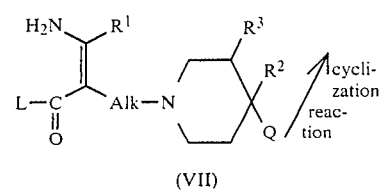

(VII)

In the formulas (IV), (V), (VI) and (VII) A, $R^1$, Alk, $R^2$, $R^3$ and Q are as previously described and L represents an appropriate leaving group such as, for example, lower alkyloxy, hydroxy, halo, amino, mono- and di(-lower alkyl)amino and the like.

The compounds of formula (I) can even so be prepared following art-known cyclizing procedures for preparing thiazolo-, 1,3,5-thiadiazolo- and dihydrothiazine rings such as, for example, by cyclizing a 2-mercaptopyrimidinone of formula (IX) with a reagent of formula (VIII-a) or, in case A is a $-C(R^4)=C(R^5)-$ radical, with a reagent of formula (VIII-b).

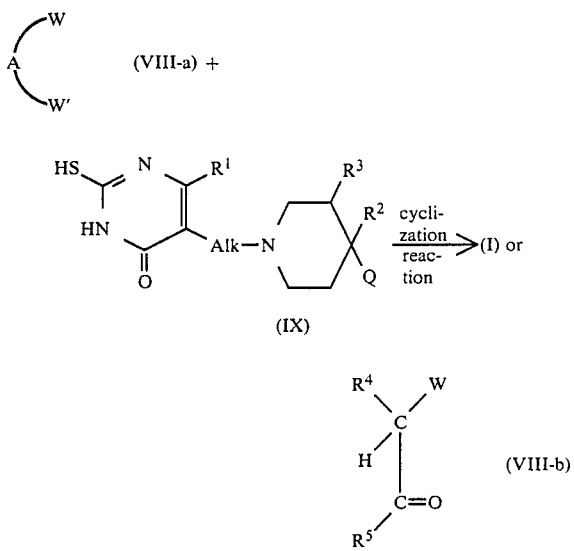

In (VIII-a) W' has the same meaning as previously described for W.

The cyclization reaction wherein the compounds of formula (I) are prepared starting from (IV) and (V), (VI) and (VII), (VIII-a) and (IX) and (VIII-b) and (IX) may generally be carried out by stirring the reactants together, if desired, in the presence of a suitable reaction-inert solvent such as, for example, an aliphatic-, alicyclic- or aromatic hydrocarbon, e.g., hexane, cyclohexane, benzene and the like; pyridine; N,N-dimethylformamide and the like amides. Elevated temperatures may be appropriate to enhance the reaction-rate. In some cases it may be preferable to carry out the reaction at the reflux temperature of the reaction mixture.

Additionally, the compounds of formula (I) can also be prepared by cyclizing an intermediate of formula (VII) with an isothiocyanate of formula (X).

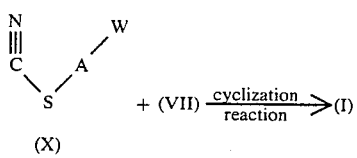

The foregoing cyclization reaction may be carried out following the same procedures as described for the preparation of (I) starting from (IV) and (V).

The compounds of formula (I) may also be converted into each other following art-known functional group-transformation procedures.

For example, the compounds of formula (I) wherein Ar—X— is an optionally substituted 2-aminobenzoyl radical, said compounds being represented by the formula (I-a), may be prepared by the oxidative cleavage of the double bond in the compound of formula (I) wherein Q is a radical of formula (b), (I-b), and subsequent hydrolysis of the thus formed amide (XI). Said oxidative cleavage may be carried out, for example, by the reaction of (I-b) with an appropriate oxidizing agent, such as, for example, sodium periodate in the presence of a catalytic amount of osmium tetroxide in a suitable solvent, e.g., 1,4-dioxane and the like. The oxidation may equally well be carried out by bubbling ozonized oxygen through a solution of (I-b) in acetic acid and subsequently decomposing the intermediately formed ozonide with water. The thus obtained amidophenylcarbonyl intermediate (XI) is then converted into (I-a) by hydrolysis in acidic medium.

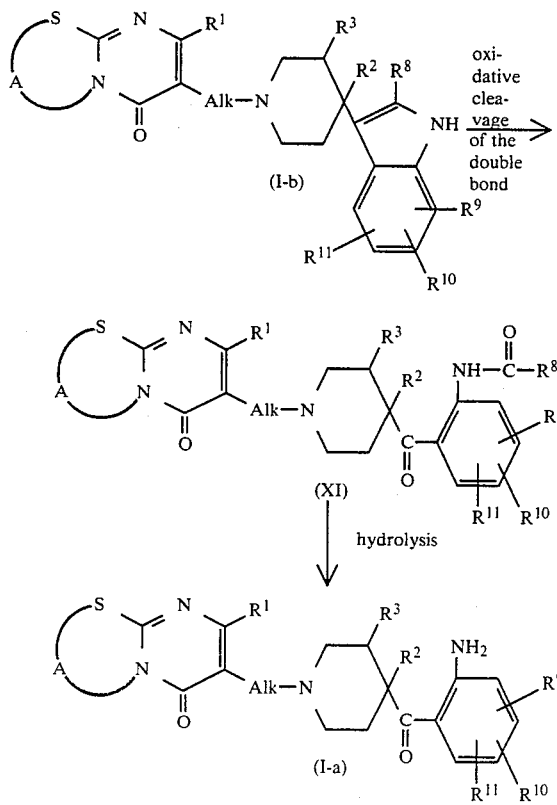

The compounds of formula (I) wherein X is a CHOH— radical (I-c), may generally be derived from the corresponding aroyl compounds, (I-d), by reducing the carbonyl group of the latter with an appropriate reducing agent, e.g., sodium borohydride, sodium cyano borohydride and the like following art-known methodologies.

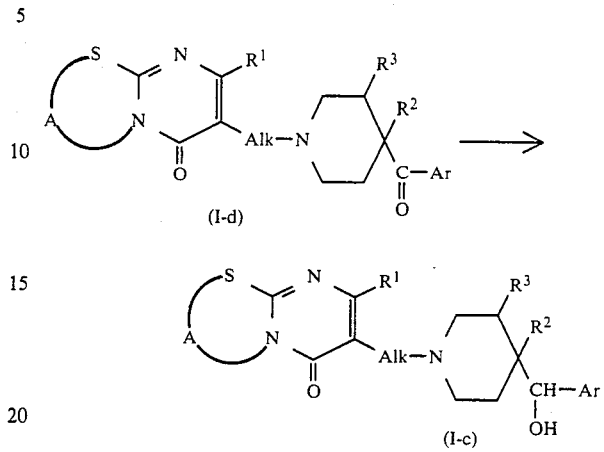

When, for example, sodium borohydride is used as a reducing agent the reaction may conveniently be carried out in alkaline aqueous medium, if desired, in admixture with a water-miscible organic solvent such as, for example, an alicyclic ether, e.g., tetrahydrofuran, 1,4-dioxane and the like; or a lower alkanol, e.g., methanol, propanol and the like.

The compounds of formula (I) wherein X represents a radical >CH—O—C(O)—$R^7$, wherein $R^7$ has the previously defined meaning, (I-e), may be derived from the corresponding alcohols (I-c) by acylating the latter with an appropriate acylating agent according to art-known procedures. Appropriate acylating agents which may be used for this purpose include lower alkanoic acids and acyl halides and anhydrides derived therefrom.

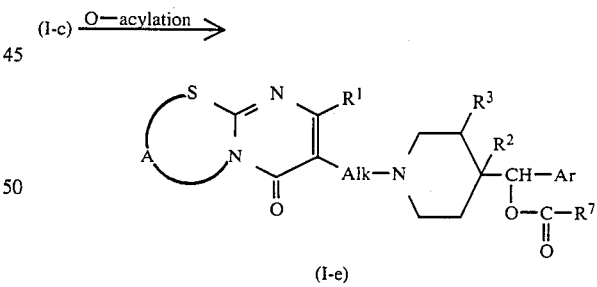

The compounds of formula (I) wherein X is a methylene radical, (I-f), may be derived from the corresponding carbonyl derivatives, (I-d), by the reduction of said carbonyl group to a methylene group, e.g., by the Clemmensen reduction, using amalgated zinc and hydrochloric acid, or by the Wolff-Kishner reduction, using hydrazine and alkali in a high-boiling polar solvent, such as, 1,2-ethanediol and the like.

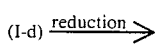

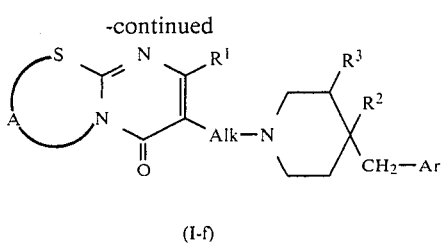

(I-f)

The compounds of formula (I) wherein X is

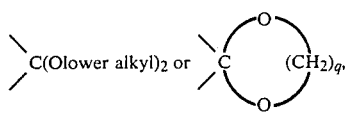

wherein said q is as previously described, may be derived from the corresponding carbonyl compounds by subjecting the latter to a ketalization-reaction following methodologies generally known in the art. Cyclic lower alkylene ketals, for example, may be prepared following methodologies analogous to those described in Synthesis, 1974, (1) 23–26.

The compounds of formula (I) wherein X represents a radical of the formula >C=NOH or a radical of the formula >C=N-NH$_2$ can easily be derived from the corresponding carbonyl compounds by reacting the latter with respectively hydroxylamine hydrochloride or hydrazine hydrochloride according to art-known procedures of preparing oximes and hydrazones.

The compounds of formula (I) have basic properties and, consequently, they may be converted to their therapeutically active non-toxic addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzensulfonic, cyclohexanesulfamic, 2-hydroxybenzoic, 4-amino-2-hydroxybenzoic and the like acids. Conversely the salt form can be converted by treatment with alkali into the free base form.

It is obvious from formula (I) that the compounds of the present invention may exist under different stereochemically isomeric forms.

The compounds of formula (I) wherein Q is a radical of formula (a), X being >CH—OH or >CH—O—C(O)—R$^7$, have at least one chiral center in their structure. This chiral center may be present in a R- and a S-configuration, this R- and S-notation being in correspondence with the rules described in R. S. Cahn, C. Ingold and V. Prelog in Angew. Chem. Int. Ed. Engl., 5, 385, 511 (1966). Consequently, the compounds of formula (I) may be present in two different enantiomeric forms, which may be separated from each other, for example, by converting the mixture of enantiomers into the acid addition salt form thereof with an optically active acid, separating the diastereomeric salts, e.g., by selective crystallization, and liberating the pure enantiomers by treatment with alkali.

When R$^3$ is other than hydrogen the piperidine ring has two asymmetric carbon atoms and each of those chiral centers may be present in a R- and S-configuration and the compounds of formula (I) may have different diastereochemical forms, resulting in a cis- and trans-configuration of the substituents on the piperidine moiety, which may be separated from each other by physical separation methods such as, selective crystallization and chromatographic techniques, e.g., counter current distribution, column-chromatography and the like techniques.

Pure stereochemically isomeric forms may also be derived from the corresponding pure stereochemically isomeric forms of the appropriate starting materials, provided that the reaction occurs stereospecifically or highly stereoselectively.

Stereochemically isomeric forms of the compounds of formula (I) are naturally intended to be embraced within the scope of the invention.

A number of the intermediates and starting materials used in the foregoing preparations are known compounds, others may be prepared according to art-known methodologies of preparing similar compounds and for some of them synthetic methods are presented hereinafter.

The intermediates of formula (II) can be prepared by converting the hydroxyl function of the corresponding alcohols (XII) into a reactive leaving group, e.g., by reacting the alcohols (XII) with thionyl chloride, sulfuryl chloride, phosphor pentabromide, phosphoryl chloride, methanesulfonyl chloride, 4-methylbenzenesulfonyl chloride and the like.

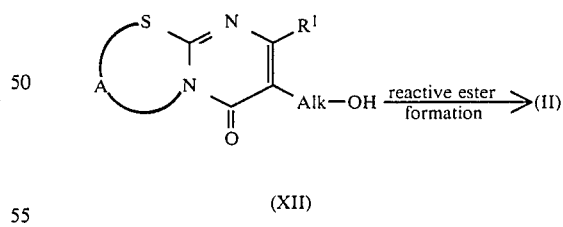

(XII)

The alcohols (XII), used as starting materials herein, may be prepared following cyclization procedures which are analogous to those described hereinabove for the preparation of (I) starting from (IV) and (V), (VI) and (VII), (VIII-a) and (IX), (VIII-b) and (IX) or (X) and (VII). Said cyclization reactions starting from (IV) and (XIII), (VI) and (XIV), (VIII-a) and (XV), (VIII-b) and (XV) and (X) and (XIV) are represented in scheme 1.

Scheme 1

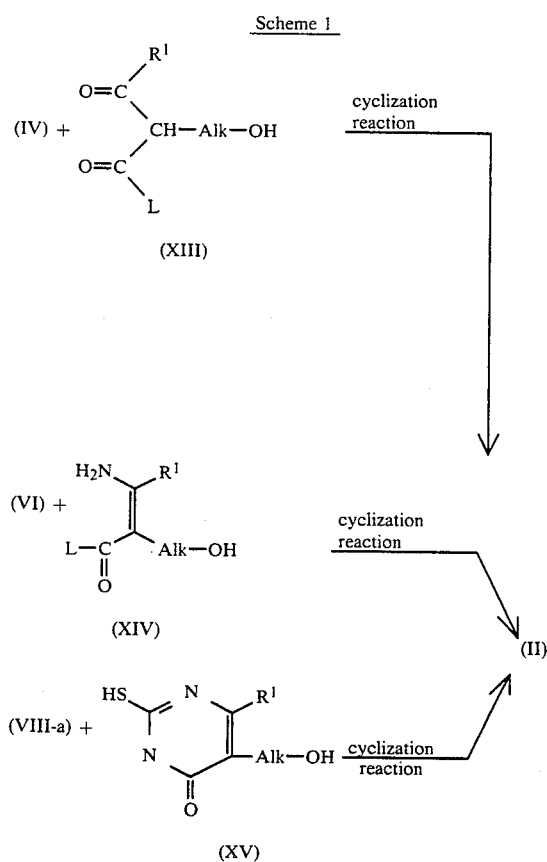

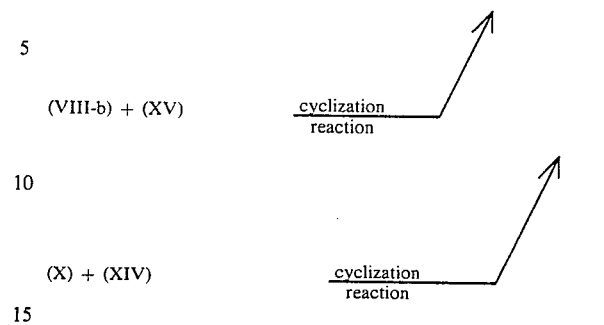

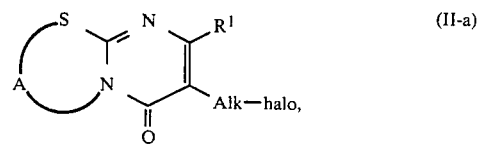

The intermediates of formula (II) wherein W is halo, said intermediates being represented by the formula $$\text{(II-a)}$$

can also be derived from (IV) and (XIII), or (VI) and (XIV), or (VIII-a) or (VIII-b) and (XV), or (X) and (XIV) in a direct way, by stirring and, if desired, heating the reactants in a suitable solvent in the presence of a suitable halogenating agent, e.g., phosphoryl chloride, thionyl chloride, phosphorpentabromide and the like. Optionally, said cyclizing and halogenating reaction can be carried out in acidic medium, e.g., in the presence of hydrogen chloride, 4-methylphenylsulfonic acid and the like acids.

The intermediates of formula (V), (VII), (XIII) and (XIV) can be derived from a compound having the formula (XVI), as shown in scheme 2.

Scheme 2

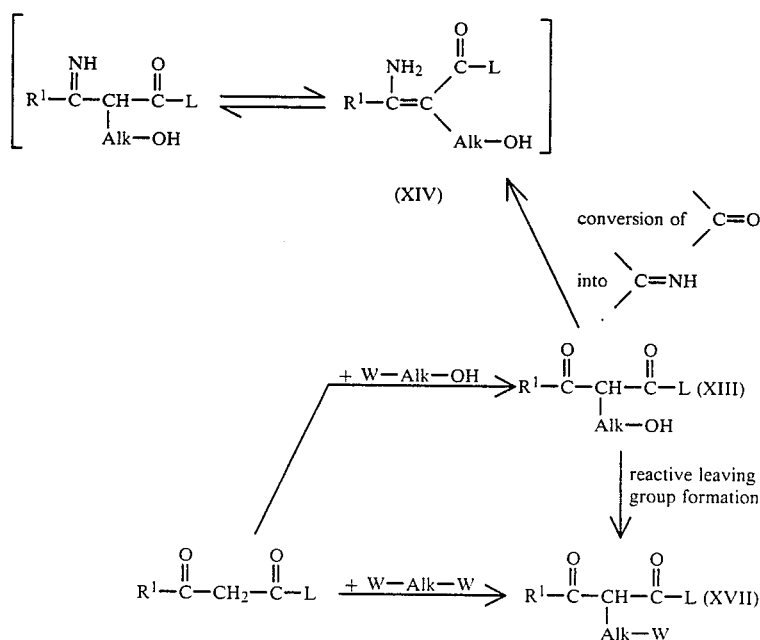

Scheme 2

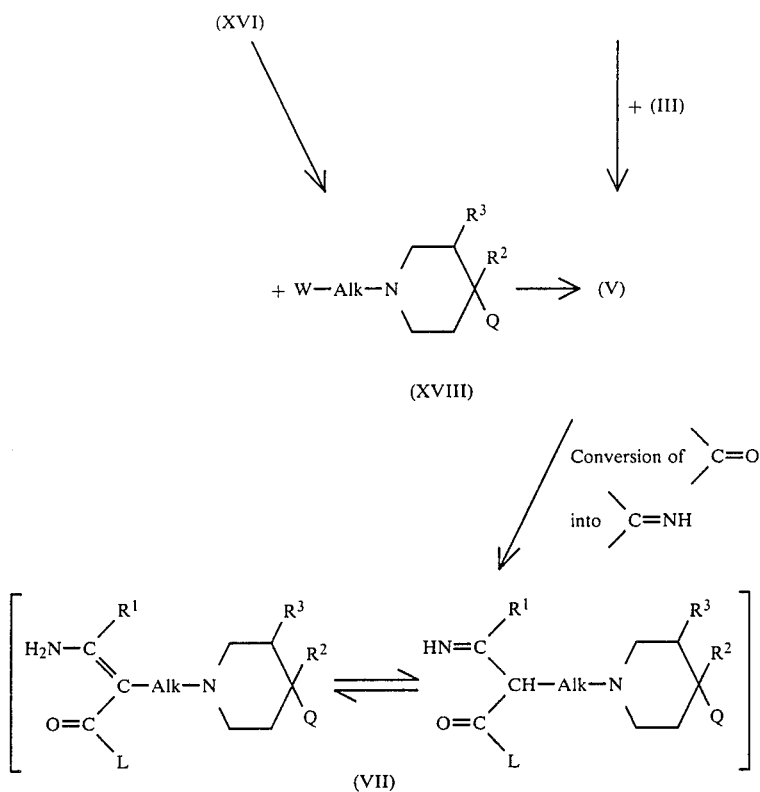

The intermediates of formula (V) can be prepared by stirring and, if desired, heating (XVI) with (XVIII) in the presence of a strong base, e.g., sodium hydride, sodium methoxide and the like in a suitable solvent. The intermediates of formula (V) can also be prepared by reacting (XVI) with a reagent of formula W—Alk—W, as described for the reaction of (XVI) with (XVIII) and, subsequently, reacting the thus obtained (XVII) with (III) following art-known N-alkylating procedures. The intermediates of formula (XVII) may also be prepared by reacting (XVI) with a reagent of formula W—Alk—OH, as described for the reaction of (XVI) with (XVIII) and, subsequently, converting the hydroxyl function in the thus obtained (XIII) into a reactive leaving group, as described hereinabove.

The intermediates of formula (XIV) and the intermediates of formula (VII) can be derived from (XIII) respectively (V) by converting the carbonyl function into an imine function, which imine may be in equilibrium with its tautomeric form.

The compounds of formula (I) and the pharmaceutical acceptable acid addition salts thereof are potent antagonists of a series of neurotransmittors and as a result they have useful pharmacological properties. For example, the compounds of formula (I) and their pharmaceutically acceptable acid addition salts possess strong psychotropic acitivity, antihistamine activity and antiserotonine activity.

The activity of the subject compounds as psychotropic agents is evidenced by the experimental data obtained in at least one of two different test procedures, viz., the combined apomorphine-, tryptamine- and norepinephrine tests in rats and the apomorphine test in dogs. The tests are carried out following the procedures described hereafter and the experimental data are summarized in table 1.

The combined apomorphine (APO)-, tryptamine (TRY)- and norepinephrine (NOR) test in rats The experimental animals used in this test were adult male Wistar rats (weight $240 \pm 10$ g). After an overnight fast, the animals were treated subcutaneously (1 ml/100 g) with an aqueous solution of the compound under investigation (time=zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures was noted. Two hours after pretreatment (time=120 minutes) finally, the same animals were challenged with 1.25 mg/kg intravenously of norepinephrine (NOR) and possible mortality was looked for up to 60 minutes later.

The table 1 gives the $ED_{50}$-values of a number of the compounds under consideration. As used herein, the $ED_{50}$-value represents the dose which protects 50% of the animals from apomorphine-, tryptamine- or norepinephrine-induced phenomena.

The apomorphine test in dogs (APO-dog)

The method used is described by P. A. J. Janssen and C. J. E. Niemegeers in Arzneim.-Forsch. (Drug Res.), 9, 765–767 (1959).

The compounds listed in table 1 were administered subcutaneously to beagle dogs at different doses and the animals were challenged 1 hour thereafter with a standard dose of 0.31 mg/kg (subcutaneous) of apomorphine.

The table 1 gives the $ED_{50}$-values of a number of the compounds under consideration. As used herein, the $ED_{50}$-value represents the dose which protects 50% of the animals from emesis.

The compounds listed in table 1 are not given for the purpose of limiting the invention thereto but only to exemplify the useful pharmacological activities of all the compounds within the scope of formula (I).

TABLE 1

| —S—A— | $R^2$ | Q | Base or Salt | $ED_{50}$(APO)-rat in mg/kg s.c. | $ED_{50}$(TRY) in mg/kg s.c. | $ED_{50}$(NOR) in mg/kg s.c. | $ED_{50}$(APO)-dog in mg/kg s.c. |
|---|---|---|---|---|---|---|---|
| —S—HC=C(CH$_3$)— | H | 4-F—C$_6$H$_4$—CO— | base | 0.16 | 0.005 | 1.25 | 0.06 |
| —S—HC=CH— | H | 4-F—C$_6$H$_4$—CO— | base | 0.02 | 0.01 | 0.63 | 0.015 |
| benzo-fused —S— | H | 4-F—C$_6$H$_4$—CO— | base | 5.0 | 0.02 | 0.31 | 1.8 |
| —S—C(CH$_3$)=N— | H | 4-F—C$_6$H$_4$—CO— | base | 2.5 | 0.31 | 0.63 | 0.50 |
| —S—CH$_2$—CH$_2$— | H | 4-F—C$_6$H$_4$—CO— | base | 0.31 | 0.16 | 0.63 | 0.03 |
| cyclopentene-fused —S— | H | 4-F—C$_6$H$_4$—CO— | base | 1.25 | 0.31 | 0.63 | 0.25 |
| —S—CH=CH— | CH$_3$ | 4-F—C$_6$H$_4$—CO— | HCl | 0.63 | 0.16 | 1.25 | 0.25 |
| —S—CH=C(CH$_3$)— | H | 1H—indol-3-yl | base | 0.08 | 0.04 | 0.16 | 0.004 |
| —S—CH=CH— | H | 1H—indol-3-yl | base | 0.08 | 0.08 | 0.31 | 0.08 |
| benzo-fused —S— | H | 1H—indol-3-yl | base | 1.25 | 0.31 | 0.16 | 0.06 |
| —S—C(CH$_3$)=N— | H | 1H—indol-3-yl | base | 5.0 | 1.25 | 0.63 | 0.06 |
| —S—CH$_2$—CH$_2$— | H | 1H—indol-3-yl | base | 1.25 | 1.25 | 1.25 | 0.008 |
| cyclopentene-fused —S— | H | 1H—indol-3-yl | base | 0.63 | 0.16 | 0.31 | 0.03 |
| —S—CH=C(CH$_3$)— | H | 5-F—1H—indol-3-yl | base | 1.25 | 0.63 | — | 0.12 |
| —S—CH=CH— | H | 5-Cl—1H—indol-3-yl | base | 0.63 | 1.25 | 1.25 | — |
| —S—CH=CH— | H | 5-F—1H—indol-3-yl | base | 1.25 | 0.31 | 1.25 | 0.12 |
| —S—CH$_2$CH$_2$CH$_2$— | H | 4-F—C$_6$H$_4$—CO— | base | 0.31 | 0.63 | 1.25 | 0.03 |
| —S—CH$_2$CH$_2$CH$_2$— | H | 1H—indol-3-yl | base | 0.63 | 0.63 | 1.25 | 0.015 |
| —S—C(CH$_3$)=C(CH$_3$)— | H | 4-F—C$_6$H$_4$—CO— | base | 0.63 | 0.04 | 0.63 | 0.12 |

TABLE 1-continued

[Structure: heterocyclic compound with S-A ring fused to N=C-N, bearing CH₃ and CH₂-CH₂-N-piperidine with R² and Q substituents, and C=O group]

| —S—A— | R² | Q | Base or Salt | ED$_{50}$(APO)-rat in mg/kg s.c. | ED$_{50}$(TRY) in mg/kg s.c. | ED$_{50}$(NOR) in mg/kg s.c. | ED$_{50}$(APO)-dog in mg/kg s.c. |
|---|---|---|---|---|---|---|---|
| —S—C=C— <br> \| \| <br> H₃C CH₃ | H | 1H—indol-3-yl | base | 0.31 | 0.16 | 0.63 | 0.015 |

The potency of the subject compounds as serotoninantagonists is clearly evidenced by the results obtained in the following tests wherein the antagonistic activity of the subject compounds on the effect of serotonin is examined.

Effects in gastric lesion tests: lesions induced by compound 48/80

Compound 48/80 (a mixture of oligomers obtained by condensation of 4-methoxy-N-methylbenzeneethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H1 antagonist. However the stimulatory effects on gastric secretion are not suppressed so that rats treated with compound 48/80 and protected from shock by an H1 antagonist may exhibit all signs of intensive gastric gland activity: gross autopsy shows distended stomachs with abnormal contents and rough bright red patches all over the mucosa, corresponding to areas of disintegrated glands. A number of known serotonin antagonists such as, for example, methysergide, cyproheptadine, cinanserin, mianserin, pipamperone, spiperone, pizotifen and metergoline, prevent completely the cyanosis of ears and extremities as well as the lesions in the glandular area of the stomach and the abnormal gastric distension. Table 2 shows for a number of compounds of formula (I) the doses (in mg/kg body weight) at which the distension of the stomach was completely absent in 50% of the test rats (ED$_{50}$-values).

Antagonistic activity on the effect of serotonin on the caudal artery of the rat Caudal arteries from fasted male rats (210–235 g) were used in the test. Two helical strips having a length of 5–6 cm and a width of 2 mm. were obtained from each artery and mounted vertically in a 100 ml organ bath containing an oxygenated Krebs-Henseleit solution. Submaximal contractions of the arterial strips were produced by adding single doses of serotonin (40 ng/ml) to the organ bath for 2 minutes with each time an interval of 10 minutes. The amplitude of the contraction was measured before and 5 minutes after adding the drug. After washing out, the agonist was added again three times in order to see whether the contraction was restored and normalized.

Table 2 shows the ED$_{50}$-values in ng/ml for a number of compounds of formula (I) and their pharmaceutically acceptable acid addition salts in the above test. In this connection the ED$_{50}$-values are the minimal concentrations of the concerned drugs which reduce the amplitude of the contraction to at least 50% of its normal value.

Inhibition of serotonin-induced contraction of guinea-pig trachea

Tracheal rings, 5 mm. long, from guinea-pigs (400–500 g, fasted overnight) were suspended with a preload of 2 g in a 100 ml tyrode-bath, gassed with a 95% O$_2$ and 5% CO$_2$ mixture (33° C.). Contractions were recorded isometrically (Statham UC2, JSI transducer amplifier, Kipp BD-9 penrecorder). A bolus of serotonin (0.31 mg/1, contact time 8 min.) was added to the bath fluid at 30 min. intervals, before and after a 30 min. incubation period with a single concentration of the antagonist. The response to the agonist in presence of the antagonist was compared with the response before the antagonist was added. (The preparation appeared unsuitable for time-activity studies). The ED$_{50}$-values, as shown in Table 2, represent the concentrations of the antagonist which reduces the effect of the agonist by 50%.

The potency of the subject compounds as histamineantagonists is evidenced by the results obtained in the following test wherein the antagonistic activity of the subject compounds on the effect of histamine is examined.

Protection of rats from compound 48/80-induced lethality

Compound 48/80, a mixture of oligomers obtained by condensation of 4-methoxy-N-methyl-phenethylamine and formaldehyde has been described as a potent histamine releasing agent (Int. Arch. Allergy, 13, 336 (1958)). The protection from compound 48/80-induced lethal circulatory collapse appears to be a simple way of evaluating quantitatively the antihistaminic activity of test-compounds. Male rats of an inbred Wistar strain, weighing 240–260 g were used in the experiment. After overnight starvation the rats were transferred to conditioned laboratories (temp.=21±1° C., relative humidity =65±5%).

The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight).

In control experiments, wherein 250 solvent-treated animals were injected with the standard dose of compound 48/80 not more than 2.8% of the animals survived after 4 hours, is therefore considered to be a safe criterion of a protective effect of drug administration.

Table 2 shows the $ED_{50}$-values in mg/kg for a number of compounds of formula (I) and their pharmaceutically acceptable acid addition salts in the above test. In this connection the $ED_{50}$-values are the minimal doses of the concerned compounds, administered in the subcutaneous way, whereby 50% of the rats are protected against compound 48/80-induced lethality.

The compounds listed in table 2 are not given for the purpose of limiting the scope of the invention but only to exemplify the useful pharmacological activities of all the compounds within the scope of formula (I).

TABLE 2

| —S—A— | $R^2$ | $R^3$ | Q | Base or Salt | gastric lesion test $ED_{50}$ in mg/kg | caudal artery rat $ED_{50}$ in ng/ml | guinea pig trachea $ED_{50}$ in ng/ml | 48/80-test $ED_{50}$ in mg/kg |
|---|---|---|---|---|---|---|---|---|
| —S—CH=C(CH₃)— | H | H | 4-F—C₆H₄—CO— | base | 0.01 | 0.32 | 0.32 | 0.31 |
| —S—CH=CH— | H | H | 4-F—C₆H₄—CO— | base | 0.005 | 0.14 | 0.18 | 0.31 |
| (benzo-fused)—S— | H | H | 4-F—C₆H₄—CO— | base | 0.08 | 0.14 | 5 | 0.16 |
| —S—C(CH₃)=N— | H | H | 4-F—C₆H₄—CO— | base | 0.0025 | 1.25 | 0.08 | 0.16 |
| —S—CH₂—CH₂— | H | H | 4-F—C₆H₄—CO— | base | 0.0005 | 0.32 | 0.16 | 0.63 |
| (cyclopentene)—S— | H | H | 4-F—C₆H₄—CO— | base | 0.04 | 0.32 | 0.32 | 0.31 |
| —S—CH=CH— | CH₃ | H | 4-F—C₆H₄—CO— | HCl | 0.005 | 0.32 | <2.5 | 0.16 |
| —S—CH—C(CH₃)— | H | H | 1H—indol-3-yl | base | 0.0025 | 0.14 | 0.63 | 0.08 |
| —S—CH=CH— | H | H | 1H—indol-3-yl | base | 0.08 | 0.08 | 0.16 | 0.02 |
| (benzo-fused)—S— | H | H | 1H—indol-3-yl | base | 0.04 | 0.32 | 5 | 0.63 |
| —S—C(CH₃)=N— | H | H | 1H—indol-3-yl | base | 0.04 | 0.56 | <0.63 | 0.04 |
| —S—CH₂—CH₂— | H | H | 1H—indol-3-yl | base | 0.04 | 0.31 | 0.31 | 0.02 |
| (cyclopentene)—S— | H | H | 1H—indol-3-yl | base | 0.31 | 0.31 | 1.25 | 0.08 |
| —S—CH=C(CH₃)— | H | H | 5-F—1H—indol-3-yl | base | 0.31 | 0.31 | — | 0.63 |
| —S—CH=CH— | H | H | 5-Cl—1H—indol-3-yl | base | 1.25 | — | — | 2.5 |
| —S—CH=CH— | C₆H₅ | H | 4-F—C₆H₄—CO | base | 2.5 | — | — | — |
| —S—CH=CH— | H | H | 5-F—1H—indol-3-yl | base | 0.08 | 1.25 | — | 1.25 |
| —S—CH₂CH₂CH₂— | H | H | 4-F—C₆H₄—CO | base | 0.01 | 0.32 | — | 0.16 |
| —S—CH₂CH₂CH₂— | H | H | 1H—indol-3-yl | base | 0.02 | 0.32 | <0.63 | 0.04 |
| —S—CH₂CH₂— | H | CH₃ | 1H—indol-3-yl | base | 2.5 | — | — | 2.5 |

TABLE 2-continued $$\begin{array}{c} \text{structure with } -S-A-, \ CH_3, \ R^3, \ R^2, \ Q, \ CH_2-CH_2-N \end{array}$$

| —S—A— | $R^2$ | $R^3$ | Q | Base or Salt | gastric lesion test $ED_{50}$ in mg/kg | caudal artery rat $ED_{50}$ in ng/ml | guinea pig trachea $ED_{50}$ in ng/ml | 48/80-test $ED_{50}$ in mg/kg |
|---|---|---|---|---|---|---|---|---|
| —S—C=C—<br>      \|  \|<br>    H₃C  CH₃ | H | H | 4-F—C₆H₄—CO | base | 0.01 | — | — | 0.08 |
| —S—C=C—<br>      \|  \|<br>    H₃C  CH₃ | H | H | 1H—indol-3-yl | base | 0.16 | 0.32 | — | 0.04 |

Due to their pharmacological activities the compounds of formula (I) and their pharmaceutically acceptable acid addition salts can be used in the treatment of psychotropic diseases and in the treatment of a variety of complaints in which serotonin release is of predominnt importance such as, for example, in the blocking of serotonin-induced contractions of bronchial tissues and of blood vessels, arteries as well as veins. The subject compounds have also useful properties as sedating-, anxiolytic-, anti-agressive-, anti-stress-, muscular protectant- and cardiovascular protectant agents and, consequently, they are useful to protect warm-blooded animals, for example, in stress situations, e.g., during transport periods and the like situations. Additionally, the subject compounds are useful as protectors of endotoxine shocks and as antidiarrhoeals.

In view of their useful pharmacological properties the subject compounds may be formulated into various pharmaceutical forms for administration purposes. To prepare the pharmaceutical compositions of this invention, a pharmaceutically effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following formulations exemplify typical pharmaceutical compositions in dosage unit form suitable for systemic administration to animal and human subjects in accordance with the present invention. These examples are given to illustrate and not to limit the scope of the present invention.

Oral Drops

The following formulation provides 50 liters of an oral-drop solution comprising 10 mg of 6-[2-[4-(1H-indol-3-yl)-1-piperidinyl]ethyl]3,7-dimethyl-5H-thiazolo[3,2-a]pyrimidin-5-one as the active ingredient (A.I.) per milliliter.

| A.I. | 500 grams |
|---|---|
| 2-hydroxypropanoic acid | 0.5 liters |
| sodium saccharin | 1750 grams |
| cocoa flavor | 2.5 liters |
| purified water | 2.5 liters |
| polyethylene glycol q.s. aq | 50 liters |

The A.I. was dissolved in the 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of the sodium saccharin in 2.5 liters of purified water and while stirring there were added the cocoa flavor and polyethylene glycol q.s. ad volume. The resulting solution was filled into suitable containers.

Oral Solution

The following formulation provides 20 liters of an oral solution comprising 20 mg of 6-[2-[4-(4-fluorobenzoyl)-1-piperidinyl]ethyl]-2,3-dihydro-7-methyl-5H-thiazolo[3,2-a]pyrimidin-5-one as the active ingredient (A.I.) per teaspoonful (5 milliliters).

| | |
|---|---|
| A.I. | 20 grams |
| 2,3-dihydroxybutanedioic acid | 10 grams |
| sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad | 20 liters. |

The methyl and propyl 4-hydroxybenzoates were dissolved in 4 liters of boiling purified water. In 3 liters of this solution were dissolved first the 2,3-dihydroxybutanedioic acid and thereafter the A.I.. The latter solution was combined with the remaining part of the former solution and the 1,2,3-propanetriol and the sorbitol solution were added thereto. The sodium saccharin was dissolved in 0.5 liters of water and the raspberry and gooseberry essences were added. The latter solution was combined with the former, water was added q.s. ad volume and the resulting solution was filled in suitable containers.

Capsules

The following formulation provides 1000 capsules comprising each 20 mg of 6-[2-[4-(1H-indol-3-yl)-1-piperidinyl]ethyl]-3,7-dimethyl-5H-thiazolo[3,2-a]pyrimidin-5-one as the active ingredient (A.I.).

| | |
|---|---|
| A.I. | 20 grams |
| Sodium lauryl sulfate | 6 grams |
| Starch | 56 grams |
| Lactose | 56 grams |
| Colloidal silicon dioxide | 0.8 grams |
| Magnesium stearate | 1.2 grams |

The composition was prepared by stirring the ingredients vigorously together. The resulting mixture was subsequently filled into suitable hardened gelatine capsules.

Film-Coated Tablets 10.000 compressed tablets, each containing as the active ingredient 10 mg of 6-[2-[4-(4-fluorobenzoyl)-1-piperidinyl]ethyl]-2,3-dihydro-7-methyl-5H-thiazolo-[3,2-a]pyrimidin-5-one, were prepared from the following formulation:

| Tablet core: | |
|---|---|
| A.I. | 100 grams |
| Lactose | 570 grams |
| Starch | 200 grams |
| Polyvinylpyrrolidone (Kollidon-K 90) | 10 grams |
| Microcrystalline cellulose (Avicel) | 100 grams |
| Sodium dodecyl sulfate | 5 grams |
| Hydrogenated vegetable oil (Sterotex) | 15 grams |
| Coating: | |
| Methyl cellulose (Methocel 60 HG) | 10 grams |
| Ethyl cellulose (Ethocel 22 cps) | 5 grams |
| 1,2,3-propanetriol | 2.5 milliliters |
| Polyethylene glycol 6000 | 10 grams |
| Concentrated colour suspension (Opaspray K-1-2109) | 30 milliliters |
| Polyvinylpyrrolidone | 5 grams |
| Magnesium octadecanoate | 2.5 grams |

Preparation of tablet core

A mixture of the A.I., the lactose and the starch was mixed well and thereafter humidified with a solution of the sodium dodecyl sulfate and the polyvinylpyrrolidone in about 200 milliliters of water. The wet powder mixture was sieved, dried and sieved again. Then there was added the microcrystalline cellulose and the hydrogenated vegetable oil. The whole was mixed well and compressed into tablets.

Coating

To a solution of the methyl cellulose in 75 milliliters of denaturated ethanol there was added a solution of the ethyl cellulose in 150 milliliters of dichloromethane. Then there were added 75 milliliters of dichloromethane and the 1,2,3-propanetriol. The polyethylene glycol was molten and dissolved in 75 milliliters of dichloromethane. The latter solution was added to the former and then there were added the magnesium octadecanoate, the polyvinylpyrrolidone and the concentrated colour suspension and the whole was homogenated.

The tablet cores were coated with the thus obtained mixture in a coating apparatus.

Injectable Solution

The following formulation provides 1 liter of a parenteral solution comprising 4 mg of 6-[2-[4-(1H-indol-3-yl)-1-piperidinyl]ethyl]-3,7-dimethyl-5H-thiazolo[3,2-a]pyrimidin-5-one as the active ingredient (A.I.) per milliliter.

| | |
|---|---|
| A.I. | 4 grams |
| Lactic acid | 4 grams |
| Propylene glycol | 0.05 grams |
| Methyl 4-hydroxybenzoate | 1.8 grams |
| Propyl 4-hydroxybenzoate | 0.2 grams |
| Purified water q.s. ad | 1 liter. |

The methyl and propyl 4-hydroxybenzoates were dissolved in about 0.5 liters of boiling water for injection. After cooling to about 50° C. there were added while stirring the lactic acid, the propylene glycol and the A.I.. The solution was cooled to room temperature and supplemented with water for injection q.s. ad volume. The solution was sterilized by filtration (U.S.P. XVII p. 811) and filled in sterile containers.

Suppositories

100 Suppositories each containing 20 mg of 6-[2-[4-(4-fluorobenzoyl)-1-piperidinyl]ethyl]-2,3-dihydro-7-methyl-5H-thiazolo[3,2-a]pyrimidin-5-one as the active ingredient (A.I.) were prepared from the following formulations:

| | |
|---|---|
| A.I. | 3 grams |
| 2.3-Dihydroxybutanedioic acid | 3 grams |
| Polyethylene glycol 400 | 25 milliliters |

| -continued | |
|---|---|
| Surfactant (Span) | 12 grams |
| Triglycerides (Witepsol 555) q.s. ad | 300 grams. |

The A.I. was dissolved in a solution of the 2,3-dihydroxybutanedioic acid in the polyethylene glycol 400. The surfactant and the triglycerides were molten together. The latter mixture was mixed well with the former solution. The thus obtained mixture was poured onto moulds at a temperature of 37°–38° C. to form the suppositories.

In view of the usefulness of the subject compounds in the treatment of psychotropic diseases it is evident that the present invention provides a method of treating warm-blooded animals suffering from psychotropic diseases, said method comprising the systemic administration of a pharmaceutically effective amount of a compound of formula (I), a pharmaceutically acceptable acid addition salt or a stereochemically isomeric form thereof in admixture with a pharmaceutical carrier.

The following examples are intended to illustrate but not to limit the scope of the present invention. Unless otherwise stated all parts herein are by weight and all temperatures are in the centigrade scale.

EXAMPLES

A. Preparation of Intermediates

EXAMPLE I

A mixture of 40 parts of 4-methyl-2-thiazolamine, 30 parts of 3-acetyl-4,5-dihydro-2(3$\underline{H}$)-furanone and 225 parts of methylbenzene was stirred and refluxed for 2.50 hours with 0.6 parts of hydrochloric acid. After cooling to room temperature, 170 parts of phosphoryl chloride were added. The whole was heated slowly to about 110° C. and stirring was continued for 2 hours at this temperature. The reaction mixture was evaporated and the residue was poured onto crushed ice. Ammonium hydroxide was added till a pH of 8 was reached. The product was extracted with trichloromethane. The extract was dried, filtered and evaporated. The residue was purified by column-chromatography over silica gel using a mixture of trichloromethane and methanol (95:5 by volume) as eluent. The pure fractions were collected and the eluent was evaporated. The residue was crystallized from a mixture of 2,2'-oxybispropane and 2-propanol, yielding 19.3 parts of 6-(2-chloroethyl)-3,7-dimethyl-5$\underline{H}$-thiazolo[3,2-a]pyrimidin-5-one (intermediate 1).

In a similar manner there were also prepared:
6-(2-chloroethyl)-2,3-dihydro-7-methyl-5$\underline{H}$-thiazolo[3,2-a]pyrimidin-5-one (intermediate 2); and
3-(2-chloroethyl)-7,8-dihydro-2-methyl-4$\underline{H}$,6$\underline{H}$-cyclopenta[4,5]thiazolo[3,2-a]pyrimidin-4-one; mp. 118° C. (intermediate 3).

EXAMPLE II

A mixture of 75 parts of 2-benzothiazolamine, 76 parts of 3-acetyl-4,5-dihydro-2(3$\underline{H}$)-furanone, 2,4 parts of a hydrochloric acid solution 12N and 270 parts of methylbenzene was stirred and refluxed for 2 hours using a water-separator. The reaction mixture was cooled and 323 parts of phosphoryl chloride were added at a temperature between 20° and 25° C. The whole was slowly heated to 110° C. and stirring was continued for 2 hours at this temperature. The solvent was evaporated and the residue was poured onto a mixture of crushed ice and ammonium hydroxide. The product was extracted with trichloromethane. The extract was dried, filtered and evaporated. The residue was purified by columnchromatography over silica gel using a mixture of trichloromethane and methanol (92:8 by volume) as eluent. The pure fractions were collected and the eluent was evaporated. The residue was crystallized from a mixture of 2-propanol and 2,2'-oxybispropane, yielding 39 parts of 3-(2-chloroethyl)-2-methyl-4$\underline{H}$-pyrido[2,1-b]benzothiazol-4-one; mp. 144° C. (intermediate 4).

In a similar manner there were also prepared:
6-(2-chloroethyl)-2,7-dimethyl-5$\underline{H}$-1,3,4-thiadiazolo[3,2-a]pyrimidin-5-one; mp. 118° C. (intermediate 5); and
6-(2-chloroethyl)-7-methyl-5$\underline{H}$-thiazolo[3,2-a]pyrimidin-5-one (intermediate 6).

EXAMPLE III

A mixture of 30 parts of 4-hydroxy-2-mercapto-6-methyl-5-pyrimidineethanol, 6.8 parts of sodium hydroxide, 15 parts of sodium hydrogen carbonate and 100 parts of 2-propanone was stirred at room temperature and there were added 180 parts of tetrahydrofuran and 170 parts of water. Then there were added at once 25 parts of 3-chloro-2-butanone and 0.2 parts of N,N,N-triethylbenzeneethanaminium chloride and the whole was stirred and heated for 1 hour at 60° C. Stirring was continued overnight at room temperature. The reaction mixture was filtered and the filtrate was salted out. The organic phase was separated, dried, filtered and evaporated, yielding 36 parts of 5-(2-hydroxyethyl)-6-methyl-2-[(1-methyl-2-oxopropyl)thio]-4(3$\underline{H}$-pyrimidinone as an oily residue (intermediate 7).

EXAMPLE IV

A mixture of 30 parts of 4-hydroxy-2-mercapto-6-methyl-5-pyrimidineethanol, 25 parts of potassium carbonate, 270 parts of N,N-dimethylacetamide and 75 parts of water was stirred at room temperature and 36 parts of 1,3-dibromopropane were added at once: temperature rises to 50° C. The whole was stirred overnight at room temperature. The reaction mixture was evaporated and water was added to the residue. The solid product was washed with water and dried in vacuo at 100° C., yielding 21 parts (58%) of 3,4-dihydro-7-(2-hydroxyethyl)-8-methyl-2$\underline{H}$,6$\underline{H}$-pyrimido[2,1-b][1,3]thiazin-6-one; mp. 155° C. (intermediate 8).

In a similar manner there was also prepared:
2,3-dihydro-6-(2-hydroxyethyl)-7-methyl-5$\underline{H}$-thiazolo[3,2-a]pyrimidin-5-one; mp. 148.7° C. (intermediate 9).

EXAMPLE V

A mixture of 20 parts of 3,4-dihydro-7-(2-hydroxyethyl)-8-methyl-2$\underline{H}$,6$\underline{H}$-pyrimido[2,1-b][1,3]thiazin-6-one, 50 parts of acetic acid and 180 parts of a hydrobromic acid solution 67% in acetic acid was stirred and heated to reflux. Stirring was continued overnight at reflux temperature. The reaction mixture was evaporated and the solid residue was triturated in 2-propanone. The product was filtered off and dried, yielding 24 parts (100%) of 7-(2-bromoethyl)-3,4-dihydro-8-methyl-2$\underline{H}$,6$\underline{H}$-pyrimido[2,1-b][1,3]thiazin-6-one monohydrobromide; mp. 215° C. (intermediate 10).

In a similar manner there was also prepared:

6-(2-bromoethyl)-2,3-dihydro-7-methyl-5H-thiazolo[3,2-a]pyrimidin-5-one monohydrobromide; mp. 237.2° C. (intermediate 11).

EXAMPLE VI

A mixture of 36 parts of 5-(2-hydroxyethyl)-6-methyl-2-[(1-methyl-2-oxopropyl)thio]-4(3H)-pyrimidinone and 240 parts of a hydrobromic acid solution 60% in acetic acid was stirred and heated for 4 hours at 90° C. The reaction mixture was evaporated and the residue was suspended in 400 parts of 2-propanone. The solid product was filtered off, washed with 2-propanone and dried, yielding 44 parts of 6-(2-bromoethyl)-2,3,7-trimethyl-5H-thiazolo[3,2-a]pyrimidin-5-one monohydrobromide; mp. 172° C. (intermediate 12).

EXAMPLE VII

To a stirred and refluxing Grignard-complex previously prepared starting from 14.6 parts of magnesium and 105 parts of 1-bromo-4-fluorobenzene in 450 parts of 1,1′-oxybisethane, was added dropwise a solution of 94 parts of 4-phenyl-1-(phenylmethyl)-4-piperidinecarbonitrile monohydrochloride in 360 parts of methylbenzene. About 250 parts of 1,1′-oxybisethane were distilled off at an internal temperature of 60°–65° C. The turbid solution was stirred and refluxed for 5 hours. The reaction mixture was decomposed with a saturate ammonium chloride solution in water. The layers were separated and the organic phase was dried, filtered and evaporated. The oily residue was boiled in a dilute hydrochloric acid solution. After cooling, the whole was alkalized with ammonium hydroxide and extracted with trichloromethane. The extract was dried, filtered and evaporated. The residue was crystallized from a mixture of 2-propanol and 2,2′-oxybispropane, yielding 91 parts (81%) of (4-fluorophenyl) [4-phenyl-1-(phenylmethyl)-4-piperidinyl]methanone; mp. 147.6° C. (intermediate 13).

Following the same Grignard-procedure there was also prepared:
(4-fluorophenyl)[4-methyl-1-(phenylmethyl)-4-piperidinyl]methanone as an oily residue (intermediate 14).

EXAMPLE VIII

To a stirred mixture of 79 parts of (4-fluorophenyl) [4-phenyl-1-(phenylmethyl)-4-piperidinyl]methanone and 630 parts of methylbenzene were added dropwise 32 parts of ethyl carbonochloridate at room temperature. Upon completion, stirring was continued for 5 hours at reflux temperature. The reaction mixture was evaporated and the (chloromethyl)benzene was distilled in vacuo (pump). The oily residue was purified by column-chromatography over silica gel using a mixture of trichloromethane and methanol (98:2 by volume) as eluent. The pure fractions were collected and the eluent was evaporated. The residue was crystallized from a mixture of 2,2′-oxybispropane and a small amount of petroleumether, yielding 35.5 parts of ethyl 4-(4-fluorobenzoyl)-4-phenyl-1-piperidinecarboxylate; mp. 91.7° C. (intermediate 15).

In a similar manner there was also prepared:
ethyl 4-(4-fluorobenzoyl)-4-methyl-1-piperidinecarboxylate as a residue (intermediate 16).

EXAMPLE IX

A mixture of 14 parts of ethyl 4-(4-fluorobenzoyl)-4-phenyl-1-piperidinecarboxylate and 150 parts of a hydrobromic acid solution 48% in water was stirred and refluxed for 30 minutes. The reaction mixture was diluted with 100 parts of water and the whole was stirred while the mixture was allowed to cool to room temperature. The precipitated product was filtered off (filtrate I was set aside), washed with methylbenzene and stirred in 2-propanone. It was filtered off again (filtrate II was set aside) and dried, yielding a first fraction of 4.3 parts of (4-fluorophenyl) (4-phenyl-4-piperidinyl)methanone hydrobromide hemihydrate.

Filtrates I and II were evaporated and the solid residue was stirred in 4-methyl-2-pentanone. The product was filtered off and dried, yielding a second fraction of 6.2 parts of (4-fluorophenyl) (4-phenyl-4-piperidinyl)methanone hydrobromide hemihydrate; mp. 173.4° C. Total yield: 73%. (intermediate 17).

In a similar manner there was also prepared:
(4-fluorophenyl) (4-methyl-4-piperidinyl)methanone hydrobromide (intermediate 18).

EXAMPLE X

To a stirred mixture of 100 parts of pyridine, 53 parts of 5-fluoro-1H-indole and 270 parts of benzene were added dropwise 57 parts of benzoyl chloride. Upon completion, stirring was continued overnight at room temperature. The reaction mixture was poured onto a dilute hydrochloric acid solution and the layers were separated. The organic phase was dried, filtered and evaporated. The residue was purified twice by column-chromatography over silica gel using a mixture of trichloromethane and methanol (95:5 by volume) as eluent. The pure fractions were collected and the eluent was evaporated, yielding 80 parts of 1-benzoyl-4-(5-fluoro-1H-indol-3-yl)-1,4-dihydropyridine as a residue (intermediate 19).

In a similar manner there was also prepared:
1-benzoyl-1,4-dihydro-4-(1H-indol-3-yl)-3-methylpyridine as an oily residue (intermediate 20).

EXAMPLE XI

A mixture of 65 parts of 1-benzoyl-4-(5-fluoro-1e,uns/H/ -indol-3-yl)-1,4-dihydropyridine and 270 parts of N,N-dimethylacetamide was hydrogenated at normal pressure and at room temperature with 10 parts of palladium-on-charcoal catalyst 10%. After the calculated amount of hydrogen was taken up, the catalyst was filtered off and the filtrate was evaporated. The residue was poured onto water and the product was extracted with 4-methyl-2-pentanone. The extract was dried, filtered and evaporated. The residue was purified by column-chromatography over silica gel using a mixture of trichloromethane and methanol (95:5 by volume) as eluent. The pure fractions were collected and the eluent was evaporated, yielding 5 parts of 1-benzoyl-4-(5-fluoro-1H-indol-3-yl)piperidine as a residue (intermediate 21).

In a similar manner there was also prepared:
cis-1-benzoyl-4-(1H-indol-3-yl)-3-methylpiperidine; mp. 230.7° C. (intermediate 22).

EXAMPLE XII

A mixture of 21 parts of cis-1-benzoyl-4-(1e,uns/H/ -indol-3-yl)-3-methylpiperidine, 60 parts of potassium hydroxide 385 parts of 1,2-ethanediol and 80 parts of water was stirred and refluxed (about 130° C.) overnight. After cooling for a while, about 200 parts of water were added whereupon the product was crystallized. The whole was further cooled and the solid product was filtered off, washed with a lot of water and with 2,2'-oxybispropane and dried, yielding 11.2 parts (80%) of cis-3-(3-methyl-4-piperidinyl)-1H-indole (intermediate 23).

In a similar manner there was also prepared:
5-fluoro-3-(4-piperidinyl)-1H-indole (intermediate 24).

B. PREPARATION OF FINAL COMPOUNDS

EXAMPLE XIII

A mixture of 3.3 parts of 6-(2-chloroethyl)-2,3-dihydro-7-methyl-5H-thiazolo[3,2-a]pyrimidin-5-one, 3 parts of (4-fluorophenyl) (4-piperidinyl)methanone hydrochloride, 8 parts of sodium carbonate and 120 parts of 4-methyl-2-pentanone was stirred and refluxed for 20 hours using a water-separator. The reaction mixture was filtered hot over Hyflo and the filter-cake was washed with trichloromethane. The filtrate was evaporated. The residue was purified by column-chromatography over silica gel using a mixture of trichloromethane and methanol (95:5 by volume) as eluent. The pure fractions were collected and the eluent was evaporated. The residue was crystallized from a mixture of 2-propanone and 2,2'-oxybispropane, yielding 2 parts of 6-[2-[4-(4-fluorobenzoyl)-1-piperidinyl]ethyl]-2,3-dihydro-7-methyl-5H-thiazolo[3,2-a]pyrimidin-5-one; mp. 165.6° C. (compound 1).

In a similar manner there were also prepared:
7-[2-[4-(4-fluorobenzoyl)-1-piperidinyl]ethyl]3,4-dihydro-8-methyl-2H, 6H-pyrimido[2,1-b][1,3]thiazin-6-one; mp. 165.2° C. (compound 2); and
3,4-dihydro-7-[2-[4-(1H-indol-3-yl)-1-piperidinyl]ethyl]-8-methyl-2H,6H-pyrimido[2,1-b][1,3]thiazin-6-one; mp. 227.1° C. (compound 3).

EXAMPLE XIV

A mixture of 3.75 parts of 6-(2-chloroethyl)-3,7-dimethyl-5H-thiazolo[3,2-a]pyrimidin-5 -one, 3.6 parts of (4-fluorophenyl) (4-piperidinyl)methanone hydrochloride, 12 parts of sodium carbonate, 0.1 parts of potassium iodide and 200 parts of 4-methyl-2-pentanone was stirred and refluxed for 22 hours using a water-separator. The reaction mixture was filtered hot over Hyflo and the filtrate was evaporated. The residue was purified by column-chromatography over silica gel using a mixture of trichloromethane and methanol (90:10 by volume) as eluent. The pure fractions were collected and the eluent was evaporated. The residue was crystallized from a mixture of acetonitrile and 2,2'-oxybispropane, yielding 5 parts of 6-[2-[4-(4-fluorobenzoyl)-1-piperidinyl]ethyl]-3,7-dimethyl-5H-thiazolo[3,2-a]pyrimidin-5-one; mp. 199.7° C. (compound 4).

Following the same procedure and using equivalent amounts of the appropriate starting materials there were also prepared:
6-[2-[4-(4-fluorobenzoyl)-1-piperidinyl]ethyl]-7-methyl-5H-thiazolo[3,2-a]pyrimidin-5-one; mp. 147.9° C. (compound 5);
3-[2-[4-(4-fluorobenzoyl)-1-piperidinyl]ethyl]-2-methyl-4e,uns/H/ -pyrimido[2,1-]benzothiazol-4-one; mp. 175.4° C. (compound 6);
6-[2-[4-(4-fluorobenzoyl)-1-piperidinyl]ethyl]-2,7-dimethyl-5H-1,3,4-thiadiazolo[3,2-a]pyrimidin-5-one; mp. 198.2° C. (compound 7);
3-[2-[4-(4-fluorobenzoyl)-1-piperidinyl]ethyl]-7,8-dihydro-2-methyl-4H,6H-cyclopenta[4,5]thiazolo[3,2-a]pyrimidin-4-one; mp. 183.8°-195.8° C. (compound 8);
6-[2-[4-(4-fluorobenzoyl)-4-methyl-1-piperidinyl]ethyl]-7-methyl-5H-thiazolo[3,2-a]pyrimidin-5-one monohydrochloride; mp. 177.1° C. (compound 9); and
6-[2-[4-(4-fluorobenzoyl)-4-phenyl-1-piperidinyl]ethyl]-7-methyl-5H-thiazolo[3,2-a]pyrimidin-5-one; mp. 161.1° C. (compound 10).

EXAMPLE XV

A mixture of 3.75 parts of 6-(2-chloroethyl)-3,7-dimethyl-5H-thiazolo[3,2-a]pyrimidin-5-one, 3 parts of 3-(4-piperidinyl)-1H-indole, 10 parts of sodium carbonate, 0.1 parts of potassium iodide and 200 parts of 4-methyl-2-pentanone was stirred and refluxed for 20 hours using a water-separator. The reaction mixture was filtered hot over Hyflo and the filtrate was evaporated. The residue was purified by column-chromatography over silica gel using a mixture of trichloromethane and methanol (90:10 by volume) as eluent. The pure fractions were collected and the eluent was evaporated. The residue was crystallized from ethanol, yielding 3.25 parts of 6-[2-[4-(1H-indol-3-yl)-1-piperidinyl]ethyl]-3,7-dimethyl-5H-thiazolo[3,2-a]pyrimidin-5-one; mp. 274.7° C. (compound 11).

Following the same procedure and using equivalent amounts of the appropriate starting materials there were also prepared:
6-[2-[4-(1H-indol-3-yl)-1-piperidinyl]ethyl]-7-methyl-5H-thiazolo[3,2-a]pyrimidin-5-one; mp. 218.5° C. (compound 12);
3-[2-[4-(1H-indol-3-yl)-1-piperidinyl]ethyl]-2-methyl-4H-pyrimido[2,1-b]benzothiazol-4-one; mp. 274.9° C. (compound 13);
6-[2-[4-(1H-indol-3-yl)-1-piperidinyl]ethyl]-2,7-dimethyl-5H-1,3,4-thiadiazolo[3,2-a]pyrimidin-5-one; mp. 260.1° C.; (compound 14);
2,3-dihydro-6-[2-[4-(1H-indol-3-yl)-1-piperidinyl]ethyl]-7-methyl-5H-thiazolo[3,2-a]pyrimidin-5-one; mp. 238.2–241.7 (dec.) (compound 15);
2-methyl-3-[2-[4-(2-methyl-1H-indol-3-yl)-1-piperidinyl]ethyl]-4H-pyrimido[2,1-b]benzothiazol-4-one; mp. 270.7° C. (compound 16);
7,8-dihydro-3-[2-[4-(1H-indol-3-yl)-1-piperidinyl]ethyl]-2-methyl-4H,6H-cyclopenta[4,5]thiazolo[3,2-a]pyrimidin-4-one; mp. 242.9° C. (compound 17);
3,7-dimethyl-6-[2-[4-(2-methyl-1H-indol-3-yl)-1-piperidinyl]ethyl]-5H-thiazolo[3,2-a]pyrimidin-5-one; mp. 187.9°–188.7° C. (compound 18);
7-methyl-6-[2-[4-(2-methyl-1H-indol-3-yl)-1-piperidinyl]ethyl]-5H-thiazolo[3,2-a]pyrimidin-5-one; mp. 170.7° C. (compound 19);
6-[2-[4-(5-fluoro-1H-indol-3-yl)-1-piperidinyl]ethyl]-3,7-dimethyl-5H-thiazolo[3,2-a]pyrimidin-5-one; mp. 270.6° C. (compound 20);
6-[2-[4-(5-chloro-1H-indol-3-yl)-1-piperidinyl]ethyl]-7-methyl-5H-thiazolo[3,2-a]pyrimidin-5-one; mp. 224.6° C. (compound 21);
6-[2-[4-(5-fluoro-1H-indol-3-yl)-1-piperidinyl]ethyl]-7-methyl-5H-thiazolo[3,2-a]pyrimidin-5-one; mp. 244.2° C. (compound 22); and
cis-2,3-dihydro-6-[2-[4-(1H-indol-3-yl)-3-methyl-1-piperidinyl]ethyl]-7-methyl-5H-thiazolo[3,2-a]pyrimidin-5-one; mp. 234.9° C. (compound 23).

EXAMPLE XVI

A mixture of 5.85 parts of 6-(2-bromoethyl)-2,3,7-trimethyl-5H-thiazolo[3,2-a]pyrimidin-5-one monohydrobromide, 4 parts of (4-fluorophenyl) (4-piperidinyl)-methanone hydrochloride, 10 parts of sodium carbonate, 3 parts of a sodium methoxide solution 30% and 240 parts of 4-methyl-2-pentanone was stirred and refluxed for 20 hours using a water-separator. The reaction mixture was filtered hot over Hyflo and the filtrate was evaporated. The residue was purified by column-chromatography over silica gel using a mixture of trichloromethane and methanol (95:5 by volume) as eluent. The pure fractions were collected and the eluent was evaporated. The residue was crystallized from a mixture of acetonitrile and 2,2′-oxybispropane (3:1 by volume) yielding 1 part of 6-[2-[4-(4-fluorobenzoyl)-1-piperidinyl]ethyl]-2,3,7-trimethyl-5H-thiazolo[3,2-a]pyrimidin-5-one; mp. 159.0° C. (compound 24).

In a similar manner there were also prepared:
6-[2-[4-(1H-indol-3-yl)-1-piperidinyl]ethyl]-2,3,7-trimethyl-5H-thiazolo[3,2-a]pyrimidin-5-one; mp. 240.2° C. (compound 25);
6-[2-[4-[(4-fluorophenyl)hydroxymethyl]-1-piperidinyl]ethyl]-3,7-dimethyl-5H-thiazolo[3,2-a]pyrimidin-5-one; mp. 138.2° C. (compound 26); and
7-[2-[4-[(4-fluorophenyl)hydroxymethyl]-1-piperidinyl]ethyl]-3,4-dihydro-8-methyl-2H,6H-pyrimido[2,1-b][1,3]thiazin-6-one; mp. 174.1° C. (compound 27).

EXAMPLE XVII

A stirred and warm suspension of 4 parts of 6-[2-[4-(1H-indol-3-yl)-1-piperidinyl]ethyl]-3,7-dimethyl-5H-thiazolo[3,2-a]pyrimidin-5-one in 80 parts of ethanol was acidified with phosphoric acid. 60 parts of water were added and the whole was boiled. The undissolved material was filtered off and the filtrate was allowed to crystallize. The product was filtered off and dried, yielding 4.5 parts (80%) of 6-[2-[4-(1H-indol-3-yl)-1-piperidinyl]ethyl]-3,7-dimethyl-5H-thiazolo[3,2-a]pyrimidin-5-one phosphate (2:3) monohydrate; mp. 214.4° C. (compound 28).

Following the same acid-addition salt formation procedure there were also prepared:
6-[2-[4-(1H-indol-3-yl)-1-piperidinyl]ethyl]-3,7-dimethyl-5H-thiazolo[3,2-a]pyrimidin-5-one sulfate (1:1) monohydrate; mp. 244.3° C. (compound 29);
6-[2-[4-(1H-indol-3-yl)-1-piperidinyl]ethyl]-3,7-dimethyl-5H-thiazolo[3,2-a]pyrimidin-5-one 2-hydroxy-1,2,3-propanetricarboxylate (2:1) monohydrate; mp. 190.5° C. (compound 30).
(+)-6-[2-[4-(1H-indol-3-yl)-1-piperidinyl]ethyl]-3,7-dimethyl-5H-thiazolo[3,2-a]pyrimidin-5-one [R-(R*,R*)]-2,3-dihydroxybutanedioate (2:1) monohydrate; mp. 177.8° C. (compound 31); and
6-[2-[4-(1H-indol-3-yl)-1-piperidinyl]ethyl]-3,7-dimethyl-5H-thiazolo[3,2-a]pyrimidin-5-one (Z)-2-butanedioate (1:1); mp. 150.6° C. (compound 32).

EXAMPLE XVIII

A mixture of 6.8 parts of 6-(2-bromoethyl)-2,3-dihydro-7-methyl-5H-thiazolo[3,2-a]pyrimidin-5-one, 3.15 parts of α-(4-fluorophenyl)-4-piperidinemethanol, 4.8 parts of sodium carbonate, 0.1 parts of potassium iodide and 200 parts of 4-methyl-2-pentanone was stirred and refluxed for 24 hours. The reaction mixture was cooled, washed with 50 parts of water, dried, filtered and evaporated. The residue was purified by column-chromatography over silica gel using a mixture of trichloromethane and methanol (90:10 by volume) as eluent. The pure fractions were collected and the eluent was evaporated. The residue solidified upon triturating in acetonitrile. The product was filtered off, washed twice with acetonitrile and dried, yielding 2.5 parts (42%) of 6-[2-[4-[(4-fluorophenyl)hydroxymethyl]-1-piperidinyl]ethyl]-2,3-dihydro-7-methyl-5H-thiazolo[3,2-a]pyrimidin-5-one; mp. 204.3° C. (compound 33).

In a similar manner there was also prepared:
cis-6-[2-[4-(1H-indol-3-yl)-3-methyl-1-piperidinyl]ethyl]-3,7-dimethyl-5H-thiazolo[3,2-a]pyrimidin-5-one; mp. 212.8° C. (compound 34).

EXAMPLE XIX

A mixture of 9.3 parts of 6-(2-bromoethyl)-3,7-dimethyl-5H-thiazolo[3,2-a]pyrimidin-5-one monohydrobromide, 6.5 parts of 4-[2-(4-fluorophenyl)-1,3-dioxolan-2-yl]piperidine, 10.2 parts of sodium carbonate and 120 parts of 4-methyl-2-pentanone was stirred and refluxed overnight. The reaction mixture was cooled and water was added. The layers were separated. The organic phase was dried, filtered and evaporated. The residue was purified by column-chromatography over silica gel using a mixture of trichloromethane and methanol (98:2 by volume) as eluent. The pure fractions were collected and the eluent was evaporated. The residue was crystallized from 2,2′-oxybispropane. The product was filtered off and dried, yielding 4 parts (35%) of 6-[2-[4-[2-(4-fluorophenyl)-1,3-dioxolan-2-yl]-1-piperidinyl]ethyl]-3,7-dimethyl-5H-thiazolo[3,2-a]pyrimidin-5-one; mp. 140° C. (compound 35).

EXAMPLE XX

A mixture of 8.3 parts of 6-[2-[4-(4-fluorobenzoyl)-1-piperidinyl]ethyl]-3,7-dimethyl-5H-thiazolo[3,2-a]pyrimidin-5-one, 10 parts of 1,1′,1″-[methylidynetris-(oxy)]trisethane, 4 parts of 4-methylbenzenesulfonic acid and 80 parts of ethanol was stirred and refluxed for 72 hours. After cooling, gaseous ammonia was introduced. The formed precipitate was filtered off and the filtrate was evaporated. The residue was purified by column-chromatography over silica gel using a mixture of trichloromethane and ethanol (90:10 by volume) as eluent. The pure fractions were collected and the eluent was evaporated. The residue was further purified by reversed phase chromatography over LiChroprep. RP 18 using a mixture of water (containing 0.5% ammonium acetate) and methanol (containing 0.1% of N-(1-methylethyl)-2-propanamine) (15:85 by volume) as eluent. The pure fractions were collected and the eluent was evaporated. The residue was crystallized from 2,2′-oxybispropane, yielding 0.6 parts of 6-[2-[4-[diethoxy(4-fluorophenyl)methyl]-1-piperidinyl]ethyl]-3,7-dimethyl-5H-thiazolo[3,2-a]pyrimidin-5-one; mp. 115.6° C. (compound 36).

What is claimed is:
1. A chemical compound having the formula

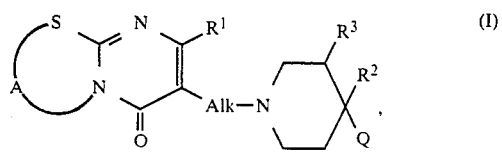

the pharmaceutically acceptable acid-addition salts and the stereochemically isomeric forms thereof, wherein:
 $R^1$ is hydrogen, lower alkyl or Ar;
 $R^2$ is hydrogen, lower alkyl or Ar;
 $R^3$ is hydrogen or lower alkyl;
 Alk is a lower alkanediyl radical;

A is a bivalent radical having the formula —CH$_2$—CH$_2$—CH$_2$—,

Q is a member selected from the group consisting of a radical having the formula —X—Ar (a) wherein X is a member selected from the group consisting of

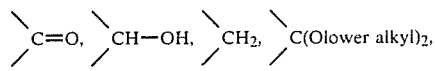

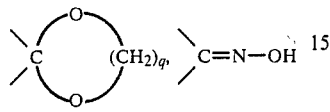

said q being the integer 2 or 3; and a radical having the formula

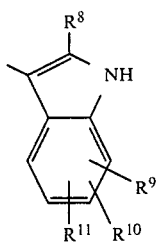

(b)

wherein $R^8$ is hydrogen or lower alkyl and $R^9$, $R^{10}$ and $R^{11}$ are each independently selected from the group consisting of hydrogen and halo; wherein Ar is phenyl or substituted phenyl, said substituted phenyl bearing an amino group and/or 1,2 or 3 halo atoms.

2. A chemical compound according to claim 1 wherein $R^1$ is lower alkyl.

3. A pharmaceutical composition for treating psychotropic diseases, comprising an inert carrier and as an active ingredient a pharmaceutically effective psychotropic amount of a chemical compound selected from the group consisting of a bicyclic pyrimidin-5-one derivative having the formula

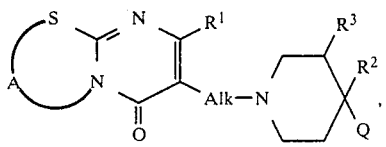

(I)

the pharmaceutically acceptable acid-addition salts and the stereochemically isomeric forms thereof, wherein:

$R^1$ is hydrogen, lower alkyl or Ar;
$R^2$ is hydrogen, lower alkyl or Ar;
$R^3$ is hydrogen or lower alkyl;
Alk is a lower alkanediyl radical;
A is a bivalent radical having the formula —CH$_2$—CH$_2$—CH$_2$—,
Q is a member selected from the group consisting of a radical having the formula —X—Ar (a) wherein X is a member selected from the group consisting of

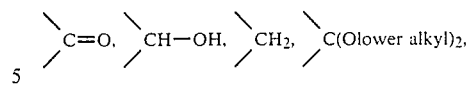

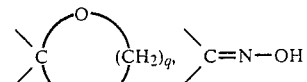

said q being the integer 2 or 3; and a radical having the formula

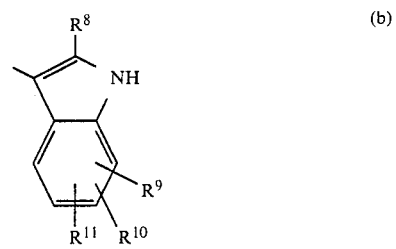

(b)

wherein $R^8$ is hydrogen or lower alkyl and $R^9$, $R^{10}$ and $R^{11}$ are each independently selected from the group consisting of hydrogen and halo; wherein Ar is phenyl or substituted phenyl, said substituted phenyl bearing an amino group and/or 1,2 or 3 halo atoms.

4. A pharmaceutical composition according to claim 3 wherein $R^1$ is lower alkyl.

5. A method of treating warm-blooded animals suffering from psychotropic diseases which comprises the administration thereto of a pharmaceutically effective psychotropic amount of a chemical compound selected from the group consisting of a bicyclic pyrimidin-5-one derivative having the formula

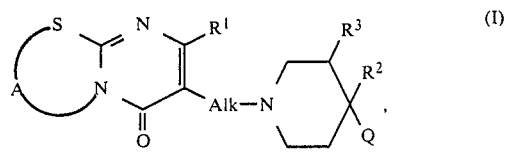

(I)

the pharmaceutically acceptable acid-addition salts and the stereochemically isomeric forms thereof, wherein:

$R^1$ is hydrogen, lower alkyl or Ar;
$R^2$ is hydrogen, lower alkyl or Ar;
$R^3$ is hydrogen or lower alkyl;
Alk is a lower alkanediyl radical;
A is a bivalent radical having the formula —CH$_2$—CH$_2$—CH$_2$—,
Q is a member selected from the group consisting of a radical having the formula —X—Ar (a) wherein X is a member selected from the group consisting of

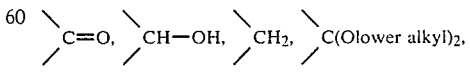

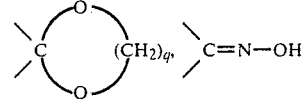

said q being the integer 2 or 3; and a radical having the formula

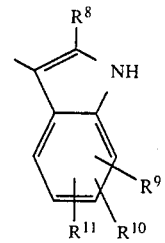

wherein $R^8$ is hydrogen or lower alkyl and $R^9$, $R^{10}$ and $R^{11}$ are each independently selected from the group consisting of hydrogen and halo;
wherein Ar is phenyl or substituted phenyl, said substituted phenyl bearing an amino group and/or 1,2 or 3 halo atoms.

6. A method according to claim 5 wherein $R^1$ is lower alkyl.

* * * * *